US00RE38088E

(19) United States
(12) Reissued Patent
Larka et al.

(10) Patent Number: US RE38,088 E
(45) Date of Reissued Patent: Apr. 22, 2003

(54) **IMMUNOASSAY FOR *H. PYLORI* IN FECAL SPECIMENS**

(75) Inventors: Christopher Vance Larka, Cincinnati, OH (US); Ching Sui Arthur Yi, Cincinnati, OH (US); Kenneth James Kozak, Cincinnati, OH (US)

(73) Assignee: Meridian Bioscience, Inc., Cincinnati, OH (US)

(21) Appl. No.: 09/500,365

(22) Filed: Feb. 8, 2000

Related U.S. Patent Documents

Reissue of:
(64) Patent No.: 5,716,791
Issued: Feb. 10, 1998
Appl. No.: 08/647,115
Filed: May 9, 1996

(51) Int. Cl.[7] ..... G01N 33/554; G01N 33/569
(52) U.S. Cl. ..... 435/7.32; 435/252.1; 435/6; 435/12; 436/66
(58) Field of Search ..... 435/7.32, 12; 436/6; 530/350; 424/186.1, 234.1

(56) References Cited

U.S. PATENT DOCUMENTS

| | | | | |
|---|---|---|---|---|
| 4,882,271 | A | 11/1989 | Evans | |
| 4,923,801 | A | 5/1990 | Marshall et al. | |
| 4,942,126 | A | 7/1990 | Slifkin | |
| 5,017,342 | A | 5/1991 | Haberzettl et al. | |
| 5,094,956 | A | 3/1992 | Grow et al. | |
| 5,262,156 | A | 11/1993 | Alemohammad | |
| 5,403,924 | A | 4/1995 | Cover et al. | |
| 5,420,014 | A | 5/1995 | Cripps et al. | |
| 5,478,926 | A | 12/1995 | Nishimura et al. | |
| 5,486,361 | A | 1/1996 | Gralnick | |
| 5,486,452 | A | 1/1996 | Gordon et al. | |
| 5,571,674 | A | * 11/1996 | Hoshina | 435/6 |

FOREIGN PATENT DOCUMENTS

| | | |
|---|---|---|
| AU | 6767690 | 6/1991 |
| CA | 1324966 | 12/1993 |
| EP | 0232085 | 1/1987 |
| EP | 0329570 | 8/1989 |
| WO | 9322682 | 11/1993 |
| WO | 9410571 | 5/1994 |
| WO | 9534677 | 12/1995 |

OTHER PUBLICATIONS

Enroth et al., *J. Clin. Microbiol.*, 33(8), pp. 2162–2165 (Aug. 1995).
Newell, D.G., *J. of Gen. Microbiol.*, vol. 133, pp. 163–170 (1987).
Price, A.B. et al., *J. Clin. Path.*, vol. 37, pp. 1007–1013 (1984) abstract.
Fox, J.G. et al., *Gastroenterology*, vol. 104, pp. 86–92 (1993).
Luzza, F. et al., *FEMS Immunol. & Med. Microbiol.*, vol. 10, pp. 285–288 (1995).
Fox, J.G. et al., *Gut. Jul.*, vol. 37, Suppl. 1, #37 (1995).
Albert, M.J. et al., *J. Med. Microbiol.*, vol. 37, pp. 176–179 (1992).
Li, C. et al., *Gastroenterology*, May 14–17, vol. 108, Suppl. #4, A147 (1995).
*Transmission of Helicobater pylori via faeces, The Lancet*, vol. 342 (Dec. 4, 1993) Leversteim–Van Hall et al.
*Meridian Releases Fifth Immunocard® Product, A Test to Detect H. Pylori*, by Meridian Diagnostics, Inc. (Dec. 13, 1994).
*Managing Peptic Ulcer Disease in the Era of Helicobacter Pylori, Paradigm, A Practical Guide*, by Health Communications, Inc., Jan. 1997.
Cutler, A.F. et al., *Treatment of Helicobacter Pylori, Gastroenterology & Endoscopy New* (Apr. 1999).
*As H. Pylori Resistance Climbs, M.D.s Urged to Guide Therapies by Drugs' Response, Gastroenterology & Endoscopy News* (Jan. 1999).
*Proton–Pump Inhibitors Cause False Negative H. Pylori Tests, Journal Watch*, vol. 18, No. 21 (Nov. 1, 1998).
*Ulcer Disease Takes Equal Toll on Women CDC Campaign Highlights Ulcer–Causing Infection that Affects Millions*, Source: Centers for Disease Control and Prevention, News Release (Nov. 19, 1998).
Correa, P. et al., *Helicobacter Pylori in Pre–Columbian Mummies* Apr. 1998.
Vaira, D. et al., *Noninvasive Tests for Monitoring Helicobacter Pylori (Hp), European Multicentre Study*, DDW/American Gastro. Assoc., Orlando, Florida (May 1999).
Peterson, J.R. et al., *Using the Helicobacter pylori Stool antigen (HpSA) in Monitoring Antibiotic Treatment Response of Helicobacter pylori, DDW/American Gastro. Assoc.*, Orlando, Florida (May 1999).
Kozak, K., *Detection of Helicobacter pylori Antigen in Stool Specimens Using a Novel Enzyme Immunoassay*, by Meridian Diagnostics, Inc., Abstract presented at The American Society for Microbiology, May 4–8, 1997.
*New Laboratory Test!!*, Premier Platinum HpSA Mar. 2000.
Rosenblatt, J.E. et al., *Evaluation of an Enzyme–linked Immunoassay (EIA) for the Detection of Helicobacter pylori Antigen in Stools*, American Society of Microbiology, Chicago, IL, (May 1999).
Braden, B. et al., *New Antigen Test in Stool Detects Helicobacter pylori Infection: Noninvasive Diagnostic Tool for Therapy Control*, DDW/American Gastro Assoc., Orlando, Florida (May 1999).

(List continued on next page.)

*Primary Examiner*—Mark Navarro
*Assistant Examiner*—Ginny Allen Portner
(74) *Attorney, Agent, or Firm*—Frost Brown Todd LLC

(57) ABSTRACT

A process for the determination of H. Pylori in a fecal specimen comprising (a) dispersing a fecal specimen suspected of carrying H. pylori in a sample diluent; (b) contacting the fecal specimen in the diluent with a first polyclonal antibody for H. pylori antigen to form a complex of the antibody and the antigen; (c) separating said specimen and said complex; (d) exposing the complex to a second polyclonal antibody for said antigen and a portion of the antibody reacting with said complex, one of said first and second antibody being bound to a solid carrier and the other being labeled with a detecting agent; and (e) determining the amount of the labeled antibody and in turn determining the presence of H. pylori antigen in said fecal specimen.

25 Claims, No Drawings

OTHER PUBLICATIONS

Hsu, Ronald K. et al., *Premier HpSA—Helicobacter pylori Stool Antigen May Detect CLO and Histology Negative Infection After Antibiotic Therapy—A Prospective Study*, DDW/American Gastro. Assoc., Orlando, Florida (May 1999).

Fanti, L. et al., *A New Simple Immunoassay for Detecting Helicobacter pylori Infection: Antigen in Stool Specimens, Digestion*, (1999) Original paper: Helicobacter pylori (Nov. 4, 1998).

Puspok, A. et al., *A new, non–invasive method for detection of Helicobacter pylori: validity in the routine clinical setting, European Journal of Gastronterology & Hepatology*, vol. 11, No. 10, pp. 1139–1142 (1999)

Bravo, L.E. et al., *Effects of Acid Suppression and Bismuth Medications on the Performance of Diagnostic Tests for Helicobacter pylori Infection, The American Journal of Gastroenterology*, vol. 94, No. 9, pp. 2380–2383 (Aug.–Sep. 1999).

Makristathis, A. et al., *Detection of Helicobacter pylori in Stool Specimens in PCR and Antigen Enzyme Immunoassay, Journal of Clinical Microbiology*, vol. 36, No. 9, pp. 2772–2774 (Sep. 1998).

Kelly, S.M. et al., *Isolation of Helicobacter pylori From Feces of Patients with Dyspepsia in the United Kingdom, Gastroenterology*, vol. 107, No. 6, pp. 1671–1674 (Dec. 1994).

*H.p. Ag—Faecal Helicobacter pylori Antigen, Quantitative Capture Elisa Test for the Dectection of Helicobacter Pylori Antigen in Stools*, by Medic, Italy (date unknown) Bib, 1999.

Marshall, B.J. et al., *Unidentified Curved Bacilli in the Stomach of Patients with Gastritis and Peptic Ulceration, The Lancet* (Jun. 1984).

*Chemical Abstracts*, vol. 124, No. 13 (Mar. 1996).

*Chemical Abstracts*, vol. 120, No. 17 (Apr. 1994).

Trevisani, L. et al., *Two Unusual Techniques for Diagnosing Helicobacter pylori Infection*, International Meeting Developing Knowledge on *Helicobacter pylori*, Gastronenterology International Congress Proceedings, vol. 10, Suppl. 4, pp. 58–60 (Dec. 1997).

*Immunodiagnostic Products and Service Catalog*, abV ImmuneResponse, Inc. (1992/1993).

*Immunochemicals '93/94*, Anawa (1993–1994).

*IMUBIND® Total uPAR ELISA Kit for measuring total uPAR antigen in human tissue extracts, plasma and tissue culture supernatants, Product #893*, American Diagnostica Inc. (1993).

The Antibody Source™ Immunological Reagents for Industry and Research, Biodesign International (1993–1994).

Thomas, J.E. et al., Abstract of Article entitled *Isolation of culture Helicobacter pylori from human faeces, Lancet*, 340 (8829), pp. 1194–1195 (Nov. 1992).

Mapstone, N.P. et al., *Abstract of Article entitled PCR identification of Helicobacter pylori in faeces from gastritis patients, Lancet*, 341 (8842), pp. 447 (Feb. 1993).

Luzzi, I., Abstract of Article entitled *Detection of vacuolating toxin of Helicobacter pylori in human faeces, Lancet*, 341 (8856), pp. 1348 (May 1993).

Van Swet, A.A. et al., Abstract of Article entitled *Use of PCR with feces for detection of Helicobacter pylori infections in patients, Lancet*, 32 (5), pp. 1346–1348 (May 1994).

Shimada, T. et al., Abstract of Article entitled *Identification of Helicobacter pylori in gastric specimens, gastric juice, saliva, and faeces of Japanese patients, Lancet*, 343 (8913), pp. 1636–1637 (Jun. 1994).

Namavar, F. et al., Abstract of Article entitled *Presence of Helicobacter pylori in the oral cavity, oesophagus, stomach and faeces of patients with gastritis, Eur. J. Clin. Microbiol. Infect. Dis.*, 14 (3), pp. 234–237 (Mar. 1995).

Sahay, P. et al., Abstract of Article entitled *Isolation of Helicobacter pylori from faeces, J. Infect.*, 30 (3), pp. 262–263 (May 1995).

Enroth, H. et al., Abstract of Article entitled *Immunomagnetic separation and PCR for detection of Helicobacter pylori in water and stool specimens, J. Clin. Microbiol.*, 33 (8), pp. 2162–2165 (Aug. 1995).

*Immunoassay Reagent Catalogue*, Biogenesis (1994–1995).

Wisdom, G.B., *Enzyme–Immunoassay, Clinical Chemistry*, vol. 22, No. 8, pp. 1243–1255 (1976).

Ahern, H., *Tools & Technology, Uses of Enzyme Immunoassays Growing in Laboratories and Clinics, The Scientist*, vol. 8, No. 3, pp. 1–6 (Feb. 1994).

Isaacson, P.G. et al., *Gene rearrangements, Helicobacter pylori, and gastric MALT lymphoma, The Lancet*, vol. 343, p. 1636 (Jun. 1994).

Banatvala, N. et al., *Identification of Helicobacter pylori in gastric specimens, gastric juice, saliva, and faeces of Japanese patients, The Lancet*, vol. 343, pp. 1636–1637 (Jun. 1994).

Thomas, J.E. et al., *Transmission of Helicobacter pylori via faeces, The Lancet*, vol. 342, pp. 1419–1420 (Dec. 1993).

Vaira, D. et al., *Diagnosis of Helicobacter pylori infection with a new non–invasive antigen–based assay, The Lancet*,, vol. 354, No. 9172, pp. 30–33 (Jul. 1999).

* cited by examiner

IMMUNOASSAY FOR *H. PYLORI* IN FECAL SPECIMENS

Matter enclosed in heavy brackets [ ] appears in the original patent but forms no part of this reissue specification; matter printed in italics indicates the additions made by reissue.

This invention relates to a method for detecting Helicobacter pylori in fetal specimens.

H. pylori is a bacterium that is found in the upper gastrointestinal tract of humans which has been implicated in gastroduodenal diseases such as peptic ulcers, gastritis and other maladies. The bacterium was originally classified as a Campylobacter and then reclassified as a Heliobacter based on more detailed information regarding its ultrastructure and fatty acid composition.

A number of different techniques, both invasive and noninvasive, have been used to detect H. pylori. The invasive techniques involve gastric biopsies and cultures. The noninvasive techniques include a urea breath test, in which the patient is given C-13 or C-14 labelled urea with a beverage, and the detection of H. pylori antibody in sera using antigens in enzyme-linked immunosorbent assays (ELISA). Examples of the latter techniques are found in U.S. Pat. No. 5,262,156 to Aleonohammad and European Patent Application 0 329 570 to Blaser.

Several major antigens have been identified and used in immunoassays in the detection of H. pylori antibodies. However, these assays have not exhibited the specificity and sensitivity that are desired in serodiagnosis. Newell, D. G., et al. Serodian. Immunother. Infec. Dis., 3:1–6 (1989). One problem with of these immunoassays in cross-reactivity. Studies of the dominant antigens in H. pylori, in particular, the putative flagellar protein, which has a molecular weight of 60 Da, have shown that some of these antigen are not specific to H. pylori and also found in other bacteria such as C. jeuni and C. coli. A second problem that has been encountered in designing immunoassays for H. pylori is strain variation. Substantial differences in the antigens has been observed in different strains of H. pylori. These problems preclude designing an assay around the use of a single antigen. The also rule out the use of monclonal antibodies. One approach that has been taken to improving the specificity and selectivity of antibody immunoassays for H. pylori has been to use a mixture of antigens from different H. pylori strains which mixture is enriched with certain antigen fragments. One ELISA which detects H. pylori antibodies in a blood sera is commercially available from Meridian Diagnostics. This assay uses a bacterial whole cell lysate as the antigen.

There are certain disadvantages to using an ELISA which employs antigens to detect the presence of H. pylori antibodies. In particular, the antibody titer in human sera remains high for a prolonged time (in some cases as much as six months) after the infection has been treated. Consequently, a positive test using this ELISA does not necessarily mean that the patient is currently infected and requires treatment for H. pylori infection. When confronted with a positive ELISA, treating physicians often order a gastric biopsy to confirm the presence of the bacteria before initiating antibiotic therapy. Therefor, the antigen-based ELISA does not eliminate the need for the invasive procedure. By contrast, if an immunoassay could be designed for detecting H. pylori antigen instead of the antibody, the need to obtain gastric biopsies to confirm infection could be reduced significantly because the antigen generally can not be detected in a patient within days of its treatment. Thus, there is a need for an ELISA which detects H.pylori antigen and, more particularly, there is a need for an ELISA for detecting H. pylori directly from fecal specimens.

While ELISA's for detecting microorganisms such as C. difficile and adenovirus in fecal specimens are known, in studies of patients with gastric biopsies which are positive for H. pylori, the bacteria ordinarily can not be cultured and isolated from the fecal specimens. This and the problems of cross reactivity and strain variation raised serious doubts that an ELISA could be designed that would be specific for H. pylori and sensitive enough to reliably detect H. pylori antigen directly from a fecal specimen.

SUMMARY OF THE INVENTION

The present invention provides a method for detecting H. pylori in fecal specimens which compares:

(a) dispersing a fecal specimen suspected of carrying H. pylori in a sample diluent;

(b) contacting the fecal specimen in the diluent with a first polyclonal antibody for H. pylori antigen to form a complex of the antibody and the antigen;

(c) separating said specimen from said complex;

(d) exposing the complex to a second polyclonal antibody for said antigen and a portion of the antibody reacting with said complex, one of said first and second antibody being bound to a solid carrier and the other being labelled with a detection agent; and (e) determining the amount of the labelled antibody and in turn determining the presence of H. pylori antigen in said fecal specimen.

In the preferred embodiment of the invention, the first antibody is bound to a carrier and the second is labelled with an enzyme. Triple sandwich assays are also provided.

The immunoassay will be supplied in the form of a kit including a plate of antibody-coated wells, sample diluent, the labeled antibody, e.g., an enzyme-antibody conjugate, wash buffer and, in the case of an ELISA, a substrate solution.

DETAILED DESCRIPTION

The immunoassay of the present invention employs polyconal antibodies for H. pylori. These antibodies can be obtained from the sera of a sensitized animal. Sensitization can be accomplished by injecting the antigen into an antibody producing species, typically a mammal and preferably a rabbit, goat or cow. Usually as initial injection is given followed by subsequent booster injections to maximize the response. Optimally, the injection regime is in multiple doses given to White New Zealand rabbits. The amount of antigen injected must be adequate to elicit a sufficient amount of antibody to be detectable. Antibody production is verified using a trial bleed and Indirect Fluorescent Assay.

H. pylori cells from ATCC strain 43504 have been found to be particularly useful in producing the polyclonal antibody. As previously mentioned, substantial strain variation has been observed in H. pylori. Differences in the organism have been observed in different geographic regions as well as dietary groups. However, antibodies obtained through sensitization using cells from strain 43504 have been found to be useful in detecting the organism across geographic regions and dietary groups. If necessary, for example, if it is found that the ELISA is not effective in detecting the organism in certain populations, cells from more than one strain of H. pylori could be used to produce the antibody.

The same labels used in known immunometric assays can be used to label the polyclonal antibody used in the present invention. Among these may be mentioned fluorogenic labels for detection by fluorimetry as described in U.S. Pat. No. 3,940,475, enzymatic markers as described in U.S. Pat. No. 3,654,090, and radioisotopes such as Iodine-125. One of the most common enzymatic markers is horseradish peroxidase (HRP) and alkaline phosphatase enzyme. Example 3 below illustrates labeling polyclonal antibodies with HRP.

The unlabeled polyclonal antibody used in the process of the present invention to extract the antigenic substance from the fecal specimen being tested can be immobilized on any of the supports commonly used in immunonmetric assays. Among these that may be used are filter paper, plastic beads, polyethylene, polystyrene, polypropylene or other suitable test tube. The techniques for bonding antibodies to such materials are well known to those skilled in the art.

To prepare the fecal specimen for use in the assay, the specimen is dispersed in a protein-based sample diluent. The diluent be formulated and buffered to minimize cross-reactivity. As examples of sample diluents, mention can be made of fetal bovine serum, normal goat serum, guinea pig serum, horse serum, casein, albumin, gelatin, and bovine serum albumin (BSA). A dilution of one part fecal specimen and four parts diluent has been found to be useful. In addition to using the protein based additives, cross-reactivity can be reduced by the addition of detergents and increasing or decreasing pH or ionic strength of the diluent buffer. For example, many sample diluents contain Triton X-100 and/or Tween 20 at concentrations ranging between 0.05% and 2%. NaCl can be added in the ranges between 0–2.9% to alter the ionic strength of the buffer system. These changes lead to greater specificity by reducing the likelihood of weak or non-specific interactions from forming.

Cross-reactivity can also be addressed in the formulation of the antibody solutions and the washes that are used in the assay. The antibody can be provided in a buffered solution in conjunction with one of the protein sera mentioned previously. The washes used in the assay can be formulated and buffered by the addition of salts and surfactants to control cross-reactivity. A preferred wash for reducing cross-reactivity is a phosphate buffered saline solution.

The preparation of the antigen, production of the polyclonal antibodies and an ELISA are illustrated in more detail by the following non-limiting examples.

EXAMPLE 1

Preparation of the Helicobacter pylori (H. pylori) antigen

H. pylori (ATCC strain 43504) was streaked for isolation on Tryptic Soy Agar (TSA) supplemented with 5% defibrinated sheep blood. The plate was incubated at 37° C. in a microaerophilic environment for 6–7 days. The resultant bacterial growth was evaluated by use of colony morphology, urease, catalase and oxidase reactions, and gram stain. Acceptable growth was subcultured to four TSA with sheep blood agar plates and grown at 37° C. in a microaerophilic environment for 3–4 days.

Each plate was flooded with 5 ml of 0.85% NaCl and the bacterial growth was harvested by a plate spreader. The bacteria were centrifuged at 10,000 xg for 15 minutes at 2°–8° C. Each pellet was resuspended in 3 ml of 0.85% NaCl and combined to one centrifuge container. The bacterial suspension was centrifuged at 10,000 xg for 15 minutes at 2°–8° C. The pellet was resuspended and centrifuged as before. The final pellet was resuspended to 3% of the total original volume in 20 mM phosphate buffer. The bacterial cells were transferred to an iced container and sonicated 5 times for 3 minutes at the maximum setting that does not cause foaming, resting for 30 seconds in between cycles. The sonicated bacterial cells were centrifuged at 57,000 xg for 15 minutes at 2°–8° C. The bacterial supernatant was collected and the pellet discarded.

EXAMPLE 2

Production of Rabbit Polyclonal

The bacterial supplement obtained in Example 1 was diluted to equal parts with Freunds complete adjuvant (total immunogen is 1.0 ml) to provide $1\times10^8$ cells per ml. This solution was mixed thoroughly and 0.2–0.5 ml of the solution was injected intramuscularly into the right hind leg and 0.1–0.25 ml of the solution was injected subcutaneously into each of eight to ten sites on the back. Subsequent injections were one month apart using Freunds incomplete adjuvant and the injection sites were limited to subcutaneous back.

A trial bleed was taken after three months. The bleed was taken from the central ear vein one week after the third injection. This bleed was incubated overnight at 2°–8° C. The next day the blood was centrifuged at 5,000 xg for 15 minutes at room temperature. The supernatant was collected and the pellet discarded. The supernatant was tested by an Indirect Fluorescent Assay (IFA). The IFA was performed by placing 10 ul of H. pylori suspension on glass slides and heat fixed. The slides were blocked with 3% bovine serum albumin (BSA) for 5 minutes then washed with a wash of phosphate buffered saline (PBS) and 0.5% Tween 20 (PBS/Tween wash). 50 ul of the trial bleeds and normal rabbit serum, as a control, diluted 1:10 in phosphate buffered saline with sodium azide (PBSA) were added and incubated in a humid environment for 30 minutes. After washing with PBS/Tween wash. Goat anti-Rabbit conjugated to FITC (fluoroescein isothiocyanate) was diluted 1:10 in PBSA and 50 ul was added to each well. The slides were incubated for 30 minutes in a dark humid environment. The slides were washed again. Fluorescene assay mounting media and a cover slip were added and viewed with a fluorescence microscope. Rabbits whose sera demonstrated a 4+ fluroescence intensity reading were then volume bled.

The volume bleed was obtained similarly to the trial bleed except 50 ml was removed from each rabbit. The blood was incubated and centrifuged as the trial bleed was.

The total volume of sera was determined and an equal volume of phosphate buffer saline (PBS) was added. A 40% ammonium sulfate precipitation was performed to remove unnecessary protein and incubated at 2°–8° C. for 24 hours. The mixture was transferred to a centrifuge tube and centrifuged at 10,000 xg for 30 minutes at room temperature. Resuspended the pellet in PBS to approximately one third of the original volume. The suspension was dialyzed against 200 times the total suspension volume of 0.175M potassium phosphate, pH 6.5 at 2°–8° C. After the dialysis, the suspension was centrifuged at 10,000 xg for 20 minutes at room temperature. The supernatant was collected and the pellet was discarded.

A DEAE (diethylaminoethyl cellulose) column was equilibrated with 0.0175M potassium phosphate, pH 6.5 at room temperature. The supernatant was placed over the column and the effluent fractions collected. A protein concentration ($OD_{280}$) was determined and all fractions greater than 0.200 were pooled. The pooled antibody was tested in the ELISA.

EXAMPLE 3

Horseradish Peroxidase Conjugation

The conjugation used 10 mg of DEAE purified rabbit anti-H. pylori antibody. The antibody was brought to a final volume of 2.5 ml by concentration or by the addition of 10 mM sodium bicarbonate pH 9.6. A PD-10 column (Pharmacia) was equilibrated with 10 mM sodium bicarbonate pH 9.6. The antibody was added to the column and nine fractions of 1.0 ml were taken. A protein concentration ($OD_{280}$E.O.=1.4) of each fraction was taken and those reading above 0.200 were pooled.

A separate PD-10 column was equilibrated with 1 mM sodium acetate trihydrate pH 4.3. The minimum amount of Horseradish Peroxidase (HRP) used was 1.172 mg HRP for each 1 mg of antibody. 1½ times the calculated minimum HRP was weighted out and added to 1.0 ml of deionized water. A protein concentrated ($OD_{403}$E.O.=2.275) was performed and HRP diluted to 10 mg/ml with deionized water. 0.1M sodium m-periodate was added at a concentration of 0.2 ml for every 4 mg HRP. This reaction was allowed to proceed for 20 minutes at room temperature with gentle rocking. The reaction was stopped by the addition of 50 ul of 2M ethylene glycol for every ml of HRP at 4 mg. The HRP was eluted through the PD-10 with 1 mM sodium acetate trihydrate pH 4.3.

The conjugation ratio was 1 mg antibody to 1.172 mg HRP. The antibody was adjusted with 10 mM sodium bicarbonate pH 9.6 and the HRP with 1 mM sodium acetate trihydrate pH 4.3. The two were combined in a dedicated flask and pH adjusted with 0.2M sodium bicarbonate, pH 9.6 to 9.6. Protected from light, the mixture was incubated for two hours on a rotator at 85–95 rpm at room temperature. After two hours, 0.1 ml of 4 mg/ml of sodium borohydride was added for every 8 mg of antibody. The new mixture was incubated at 4° C. for two hours on a rotator. The conjugate was passed through a PD-10, equilibrated with PBS, and fractions containing the conjugate were collected. The fractions wee pooled and concentrated to approximately 1.0 ml. The concentrate was placed over a Sephracryl S-200 column equilibrated with PBS at a flow rate of 10 ml/hr. 2.0 ml fractions were collected and a protein concentration of both the antibody and the HRP were performed. The fractions with a simultaneous peak in both the $OD_{280}$ and $OD_{403}$ were pooled and concentrated to approximately 1.0 mg/ml.

Example 4 below illustrates a so called "forward" assay in which the antibody bound to the support is first contacted with the specimen being tested to extract the antigen from the sample by formation of an antibody/antigen complex and contacting the complex with a known quantity of labelled antibodies. However, those skilled in the art will appreciate that the immunometric assay can also be conducted as a so called "simultaneous" or "reverse" assay. A simultaneous assay involves a single incubation step as the antibody bound to the solid support and the labelled antibody are both added to the sample being tested at the same time. After the incubation is complete, the solid support is washed to remove the residual sample and uncomplexed labeled antibody. The presence of the labeled antibody associated with the solid support is then determined. A reverse assay involves the step wise addition first of a solution of labeled antibody to the fecal specimen followed by the addition of the unlabeled antibody bound to the support. After a second incubation, the support is washed in a conventional fashion to free it of the residual specimen and the unreacted labelled antibody.

EXAMPLE 4

ELISA Test

The antibody was diluted to PBS serially between 20 ug/ml and 2.5 ug/ml. A 0.100 ml aliquot of each dilution was added to an Immunlon-II strip (Dynatech), covered and incubated overnight at room temperature. The plate was washed once with PBS/Tween wash. It was blocked with 1%BSA/PBS for 1 hour at room temperature. Again washed once with PBS/Tween wash. Several positive and negative samples were diluted 1:5 in 0.1%BSA/PBS. Each sample (0.100 ml) was added to a well of the strips, covered and incubated 1 hour at room temperature. The plate was then washed 5 times with Merifluor C/G wash. A previously accepted rabbit anti-H. pylori conjugated to horseradish peroxidase was diluted to 10 ug/ml and 0.100 ml added to each well. The plate was covered and incubated at room temperature for 1 hour. Again washed 5 times with PBS/Tween wash then developed for 10 minutes at room temperature with 0.100 ml of trimethylbensidine (TMB) solution. Stopped with 0.050 ml $2NH_2SO_4$ and read after two minutes. The dilution yielding the maximum signal and lowest background was chosen as the optimal dilution.

Quantitative determinations can be made by comparing the measure of labeled antibody with that obtained for calibrating samples containing known quantities of antigen. Table 1 below shows the optical density obtained when four samples, each containing a predetermined number of organisms, is run through the assay.

TABLE 1

| No. of organisms per ml | $OD_{450/630}$ |
|---|---|
| $3 \times 10^7$ | 2.547 |
| $1.9 \times 10^7$ | 0.662 |
| $4.6 \times 10^6$ | 0.182 |
| $1.1 \times 10^6$ | 0.038 |

The results of running six clinical specimens through the assay are shown in Table 2.

| Sample | $OD_{450/630}$ | Result |
|---|---|---|
| 1 | 0.301 | Positive |
| 2 | 0.713 | Positive |
| 3 | 0.284 | Positive |
| 4 | 0.005 | Negative |
| 5 | 0.033 | Negative |
| 6 | 0.008 | Negative |

So-called triple sandwich assays can also be used for detecting H. pylori in fecal specimens in accordance with the invention. Triple assays are know in the art and the basic methodology can be applied to the detection of H. pylori in fecal specimens. A triple assays is typically conducted by dispersing a fecal specimen suspected of carrying H. pylori in a sample diluent which minimizes cross-reactivity and adding the diluted sample to an immobilized antibody for H. pylori that has been obtained from a first species of an antibody producing animal. The sample is incubated to form the antibody-antigen complex. After washing excess specimen from the immobilized support, an H. pylori antibody known as a primary antibody and obtained from a second species of an antibody producing animal is added to the antibody-antigen complex and incubated to form an antibody-antigen-antibody complex. After forming this complex and removing the unreacted antibody, the complex is reacted with an antibody known as a secondary antibody which is an antibody to the second antibody producing species such as anti-(rabbit, cow or goat) immunoglobulin. The secondary antibody is labelled in a conventional manner, typically with an enzyme, and incubated with the antibody-antigen-antibody complex to form a triple antibody complex or sandwich. After removing the unreacted secondary antibody, the antigen is assayed in a conventional manner. In using an enzyme label, a substrate is added to the complex of the antigen and the three antibodies and the reaction of the substrate with the linked enzyme is monitored to determine the amount of the antigen present in the specimen. In the triple sandwich assay, as in the basic sandwich assay, the washes and the antibody solutions are formulated or buffered to control cross-reactivity as needed.

Having described the invention in detail and by reference to the preferred embodiments it will be apparent to those skilled in the art that modifications and variations are possible without departing from the scope of the invention as defined in the following appended claims.

What is claimed is:

1. A process for determination of H. pylori in a fecal specimen which comprises:

(a) dispersing a fecal specimen suspected of carrying H. pylori in a sample diluent;

(b) contacting the fecal specimen in the diluent with a first polyclonal antibody for H. pylori antigen to form a complex of the antibody and the antigen;

(c) separating said specimen and said complex;

(d) exposing the complex to a second polyclonal antibody for said antigen and a portion of the antibody reacting with said complex, one of said first and second antibody being bound to a solid carrier and the other being labelled with a detection agent; and (e) determining the amount of the labelled antibody and in turn determining the presence of H. pylori antigen in said fecal specimen.

2. The process of claim 1 wherein the first antibody is bound to a solid carrier and the second antibody is labelled with a detection agent.

3. The process of claim 1 wherein the first antibody is labelled with a detection agent and the second is bound to a solid carrier.

4. The process claim 1 wherein the sample diluent is a protein based diluent.

5. The process of claim 1 wherein said polyclonal antibody is obtained by sensitizing an antibody-producing mammal with H. pylori cells.

6. The process of claim 4 wherein the sample diluent contains a protein selected from the group consisting of fecal bovine serum, normal goat serum, guinea pig serum, horse serum, casein, albumin, gelatin, and bovine serum albumin.

7. The process of claim 1 wherein after exposing the complex to the second antibody, the complex is washed with a buffer that reduces cross-reactivity or otherwise improves the specificity of the assay.

8. The process of claim 5 wherein the cells are cells from a plurality of H. pylori strains.

9. The process of claim 3 wherein said detection agent is selected from the group consisting of alkaline phosphatase and beta galactosidase horseradish peroxidase.

10. The process of claim 7 wherein said wash is phosphate buffered saline.

11. The process of claim 5 wherein said cells are cells from ATCC strain 43504.

12. A process for the determination of H. pylori in a fecal specimen which comprises:

(a) dispersing a fecal specimen suspected of carrying H. pylori in a sample diluent;

(b) contacting the fecal specimen in the diluent with a first polyclonal antibody for H. pylori antigen bound to a solid carrier and a second labelled polyclonal antibody for H. pylori to form a complex of the antibodies and the antigen;

(c) separating said specimen and said complex;

(d) determining the amount of the labelled antibody and in turn determining the presence of H. pylori antigen in said fecal specimen.

13. A process for the determination of H. pylori in a fecal specimen which comprises:

(a) dispersing a fecal specimen suspected of carrying H. pylori in a sample diluent;

(b) contacting the fecal specimen in the diluent with a first polyclonal antibody for H. pylori antigen produced by a first antibody-producing species and bound to a solid carrier to form a complex of the antibody and the antigen;

(c) separating said specimen and said complex;

(d) contacting the antibody-antigen complex formed in step (b) with a primary polyclonal antibody for H. pylori antigen obtained from a second antibody-producing species to produce a antibody-antigen-antibody complex;

(e) removing the primary antibody not present in the complex from step (d);

(f) contacting the antibody-antigen-antibody complex formed in step (d) with a secondary antibody, said secondary antibody being an antibody for the second antibody-producing species, whereby said secondary antibody forms a complex with said antibody-antigen-antibody complex; and (g) determining the presence of H. pylori antigen in said fecal specimen.

*14. A process for the determination of H. pylori in a fecal specimen which comprises:*

*(a) dispersing a fecal specimen suspected of carrying H. pylori in a sample diluent;*

*(b) contacting the fecal specimen in the diluent with a first polyclonal antibody for H. pylori antigen to form a complex of the first polyclonal antibody and the antigen;*

*(c) separating said specimen and said complex;*

*(d) exposing the complex to a second polyclonal antibody for said antigen and a portion of the second polyclonal antibody reacting with said complex, one of said first and second polyclonal antibody being bound to a solid carrier and the other being labeled with a detection agent; and*

*(e) determining the presence in said complex of the antibody labeled with the detection agent and in turn determining the presence of H. pylori antigen in said fecal specimen.*

*15. The process of claim 14 wherein the first antibody is bound to a solid carrier and the second antibody is labeled with a detection agent.*

*16. The process of claim 14 wherein the first antibody is labeled with a detection agent and the second is bound to a solid carrier.*

*17. The process of claim 14 wherein the sample diluent is a protein based diluent.*

*18. The process of claim 14 wherein said polyclonal anti-body is obtained by sensitizing an antibody-producing mammal with H. pylori cells.*

*19. The process of claim 17 wherein the sample diluent contains a protein selected from the group consisting of fecal bovine serum, normal goat serum, guinea pig serum, horse serum, casein, albumin, gelatin, and bovine serum albumin.*

*20. The process of claim 14 wherein after exposing the complex to the second antibody, the complex is washed with a buffer that reduces cross-reactivity or otherwise improves the specificity of the assay.*

*21. The process of claim 18 wherein the cells are cells from a plurality of H. pylori strains.*

*22. The process of claim 17 wherein said detection agent is selected from the group consisting of alkaline phosphatase and beta galactosidase horseradish peroxidase.*

*23. The process of claim 20 wherein said wash is phosphate buffered saline.*

*24. The process of claim 18 wherein said cells are cells from ATCC strain* 43504.

*25. A process for the determination of H. pylori in a fecal specimen which comprises:*

(*a*) *dispersing a fecal specimen suspected of carrying H. pylori in a sample diluent;*

(*b*) *contacting the fecal specimen in the diluent with a first polyclonal antibody for H. pylori antigen bound to a solid carrier and a second labeled polyclonal antibody for H. pylori antigen to form a complex of the first and second antibodies and the antigen;*

(*c*) *separating said specimen and said complex;*

(*d*) *determining the presence in said complex of the labeled antibody and in turn determining the presence of H. pylori antigen in said fecal specimen.*

* * * * *